United States Patent
Kirsch et al.

(10) Patent No.: US 7,474,777 B2
(45) Date of Patent: Jan. 6, 2009

(54) DEVICE AND METHOD FOR OPTICAL MEASUREMENT OF CHEMICAL AND/OR BIOLOGICAL SAMPLES

(75) Inventors: Achim Kirsch, Hamburg (DE); Roland Stange, Hamburg (DE); Jürgen Müller, Hamburg (DE)

(73) Assignee: Evotec Oai AG, Hamburg (DE)

( * ) Notice: Subject to any disclaimer, the term of this patent is extended or adjusted under 35 U.S.C. 154(b) by 452 days.

(21) Appl. No.: 10/476,243

(22) PCT Filed: Apr. 26, 2002

(86) PCT No.: PCT/EP02/04623

§ 371 (c)(1),
(2), (4) Date: Aug. 12, 2004

(87) PCT Pub. No.: WO02/088819

PCT Pub. Date: Nov. 7, 2002

(65) Prior Publication Data

US 2004/0257576 A1    Dec. 23, 2004

(30) Foreign Application Priority Data

Apr. 28, 2001    (DE) .................. 101 21 064

(51) Int. Cl.
*G06K 9/00* (2006.01)
*G01N 21/00* (2006.01)
(52) U.S. Cl. ...................... 382/129; 356/436
(58) Field of Classification Search ......... 382/128–134; 250/255, 288, 339.11, 339.12, 339.13, 341.8, 250/425, 461.2, 591.1; 436/63, 64, 172; 356/36, 244, 300, 311, 317, 342, 407, 408, 356/417, 440, 484, 941
See application file for complete search history.

(56) References Cited

U.S. PATENT DOCUMENTS

| | | | |
|---|---|---|---|
| 4,283,112 A | | 8/1981 | Venable |
| 4,844,617 A | | 7/1989 | Kelderman et al. |
| 5,384,455 A | * | 1/1995 | Paxman .................. 250/201.9 |
| 5,508,844 A | | 4/1996 | Blake |
| 5,583,632 A | * | 12/1996 | Haga ........................ 356/129 |
| 5,635,402 A | * | 6/1997 | Alfano et al. ................ 436/63 |
| 5,659,642 A | | 8/1997 | King et al. |
| 5,813,987 A | * | 9/1998 | Modell et al. .............. 600/473 |
| 5,981,956 A | * | 11/1999 | Stern ...................... 250/458.1 |
| 6,025,601 A | * | 2/2000 | Trulson et al. .......... 250/461.2 |
| 6,084,670 A | * | 7/2000 | Yamazaki et al. ........... 356/343 |

FOREIGN PATENT DOCUMENTS

DE    3328821 A1    2/1985

(Continued)

OTHER PUBLICATIONS

Brock, Roland, "Fluorescence Correlation Microscopy and quantitative Microsphere Recruitment Assay", dissertation, 1999, 175 pp.

(Continued)

*Primary Examiner*—Abolfazl Tabatabai
(74) *Attorney, Agent, or Firm*—Griffin & Szipl, P.C.

(57) ABSTRACT

An optical measurement device for measurement of chemical and/or biological samples comprises an illumination means (16) for illuminating the sample (20) to be measured. Further, an optics means (22) is provided for imaging a sample area in an image field (10). A first partial area (12) of the image field is covered by a first detector (28), and a second partial area (14) of the image field (10) is covered by a second detector (34). Thus, it is possible to change between two measurement methods without switching or to perform two measurements on a sample at the same time.

22 Claims, 8 Drawing Sheets

FOREIGN PATENT DOCUMENTS

| | | |
|---|---|---|
| DE | 43 30 347 C2 | 3/1995 |
| DE | 197 28 966 A1 | 10/1998 |
| DE | 197 48 211 A1 | 5/1999 |
| DE | 199 19 092 A1 | 11/2000 |
| DE | 199 36 999 A1 | 3/2001 |
| EP | 0782027 A2 | 7/1997 |
| GB | 2181538 A | 4/1987 |
| GB | 2181538 A | 4/1987 |
| JP | 06174433 | 6/1994 |
| JP | 10-307252 | 11/1998 |

OTHER PUBLICATIONS

McNamara, Kerry P. et al, "Dynamic analytical chemistry: a kinetic study of the labeling of normal and age fractionated human erythrocytes with monobromobimane", Analytica Chimica Acta, 356 (1997) pp. 75-83.

German Examination Report, dated Oct. 15, 2001.

International Search Report, completed Jan. 24, 2003.

International Preliminary Examination Report, completed Aug. 8, 2003.

Patent Abstracts of Japan, vol. 1999, No. 02, Feb. 26, 1999.

English Translation of International Preliminary Examination Report.

* cited by examiner

DEVICE AND METHOD FOR OPTICAL MEASUREMENT OF CHEMICAL AND/OR BIOLOGICAL SAMPLES

This is a National Phase Application in the United States of International Patent Application No. PCT/EP02/04623, filed Apr. 26, 2002, which claims priority on German Patent Application No. 10121064.7, filed Apr. 28, 2001. The entire disclosures of the above patent applications are hereby incorporated by reference.

FIELD OF THE INVENTION

The invention relates to a device and a method for optical measurement of chemical and/or biological samples. The inventive device and the inventive method are particularly suited for use in high and medium throughput screening systems.

BACKGROUND OF THE INVENTION

For the microscopic optical examination of samples, various measurement methods exist which provide different kinds of information. Either image or point measurements can be performed. In image measurements, generally, the value of a physical quantity is recorded in dependence on the measurement site. The measurement of this physical quantity is performed either at numerous different points or measurement sites in parallel, or respectively only at one point, and the site of this point, i.e. the measurement site, will be varied. The latter is often referred to as a "screening" of the sample surface. In this case, each individual measurement has to be performed very fast so that the image measurement can be concluded within an acceptable length of time.

Examples of useful image measurement methods are: bright-field, dark-field, total-internal-reflection, fluorescence, 2-photon-fluorescence, fluorescence-lifetime, fluorescence-emission-spectroscopy, polarization and fluorescence-polarization microscopy. Further, these methods can be performed by use of different detectors such as e.g. line cameras or surface cameras, and, in part, these detectors can be used both in conventional and confocal arrangements.

In point measurements, contrary to image measurement, the measurement is carried out only at one site on the sample, or the site information is not evaluated, or an averaging including a large number of measurement sites is performed (conventional measurement by use of a large-surfaced detector). Correspondingly, the individual measurement may be both more complex and more time-consuming. The complexity can relate both to the measurement apparatus and the data obtained (e.g. complete spectra). For instance, in the fluorescence correlation spectroscopy (FCS) point measurement method, the fluctuation of a fluorescence signal coming from a small volume is recorded over a longer period of time, and the signal is used to derive information on photophysical, chemical and physical properties of fluorescent particles and molecule in this volume. In these measurements, it is often assumed beforehand that the volume observed is representative of the sample. This will of course largely apply to homogenous samples but only to a restricted extent if also structured components occur in the sample. Useful point measurement methods are—although the following examples are not exhaustive—FCS, FIDA, fluorescence-emission, fluorescence-excitation and fluorescence-absorption spectroscopy, fluorescence-lifetime spectroscopy and fluorescence-anisotropy measurements, as described in numerous scientific and technical publications. The measurements can often be performed both in a conventional and a confocal arrangement.

For the characterization of substances with regard to possible pharmaceutical and medical uses, it is often reasonable and necessary to carry out an examination by use of image and point measurement methods alike. Then, information on all components can be extracted from samples containing homogeneous as well as structured components. By way of example, it could be examined in what manner a sample comprising cells which are assumed to release certain molecules into the solution surrounding them, will react on an added test substance. With the FCS method, the possible occurrence of a biochemical reaction in the solution can be detected while fluorescence microscopy makes it possible to examine the cell layer and to obtain indications e.g. of a possible toxic nature of the test substance.

In multi-channel microscopy, a sample can be subjected to imaging measurement methods for performing a plurality of measurements of the same sample region under different measurement conditions or with different detectors. Thereby, for instance, there is determined the distribution of different fluorophobes in the sample, which differ from each other with regard to their photophysical properties such as e.g. the excitation and emission spectra and/or the fluorescence lifetime.

As to the devices wherein image measurement methods are combined with point measurement methods, mention should be made of the FCS apparatus for intracellular FCS by Brock (see e.g. Brock, "Fluorescence Correlation Microscopy and Quantitative Microsphere Recruitment Assay", dissertation, 1999). This apparatus comprises a fluorescence microscope which has been retrofitted to include the components required for FCS. The selection among the measurement methods of microscopy or FCS is realized by a hinged mirror arranged in the path of rays.

To begin with, such a mechanical switching of the path of rays by means of a hinged mirror entails the necessity to determine the positions of the different measurement volumes relative to each other. High-throughput applications are subject to the additional necessity to perform this switching cycle a large number of times, thus causing mechanical wear of the constructional components. This wear process particularly affects a predefined relative position of the measurement volumes so that this position would have to be redefined at regular intervals. In certain cases, even the complete switching unit has to be replaced because of wear. Especially in high-throughput applications, a disadvantage is caused by the loss of measurement time due to the switching process, resulting in a decrease of the obtainable sample throughput.

So-called laser scanning microscopes (LSM) generate a two-dimensional image of a sample by sequential screening of the object plane with a single small measurement volume. Based on the knowledge on the position of the measurement volume at each point of time and on the corresponding picked-up measurement value, an image of this plane can be generated. Possible signals for this purpose include reflection and fluorescence intensity but also anisotropy and fluorescence anisotropy. In microscopes of the above type, a combination with point measurement methods such as e.g. the fluorescence emission spectroscopy is relatively simple since only the movement of the measurement volume need be eliminated for obtaining a sufficient measurement time.

When using laser scanning microscopes, a disadvantage resides in the relatively long measurement times for the individual images. A use of such microscopes for high-throughput screening will thus not be possible because the required short measurement times with sufficient signal quality cannot be obtained. In short measurement times, the measurement results will have only a small signal-to-noise ratio, so that an averaging has to be performed over several images. This averaging is carried out for improving the signal-to-noise ratio and therefore is necessary in case of short measurement times for an individual image. In case of long measurement times, a sufficient signal-to-noise ratio can be obtained also without averaging. This in turn will increase the measurement time. Further, the laser scanning microscope is restricted to the use of relatively complex image-generating methods.

To be able to distinguish a plurality of fluorophores in a microscope on the basis of their excitation and emission spectra, special optical filters, chromatic cameras and imaging spectrographs are used in multi-channel microscopes.

Normally, when optical filters are used, at least three filters will be employed. The first filter determines the excitation wavelength range, the second filter is a dichromatic mirror which reflects the excitation light and transmits the emission light (or vice versa). In front of the detector, a further filter is inserted, transmitting only the emission range. For the detection of different fluorophores, the possibility exists to exchange all three filters, according to the standardized routine when using commercially available microscopes. Alternatively, a single filter set can be arranged for a plurality of colorants if the excitation and emission wavelengths are sufficiently remote from each other, as is the case e.g. for the colorants DAPI, FITC and TRITC. If these colorants have to be recorded separately, a color film or a color CCD camera can be used. Likewise suited is a monochrome camera in combination with a selectable excitation spectrum, as performed e.g. in the so-called Pinkel filter sets. Filter sets also offer the opportunity to distinguish colorants from each other on the basis of their Stokes shift. In this manner, different colorants can be excited by the same wavelength and will differ from each other by the different displacement of the emission spectrum.

In multi-channel microscopes, it is frequently required to exchange one or several filters between the individual measurements. When using high-throughput systems, this causes considerable disadvantages, such as e.g. wear of components or losses in measurement time due to the switching times. Systems adapted to detect a plurality of colorants simultaneously are restricted to mere few combinations of colorants because the emission spectra must be sufficiently different and must not overlap with the excitation spectra of the other colorants. Further, the manufacture of such optical filters which are suited for a plurality of colorants is very complex so that a change towards other colorants is impeded by the considerable expenses for development and manufacture. This imposes heavy restrictions on the selection of the possible colorants. This disadvantage affects also systems which are based on spectrographs since also these require that the excitation light be attenuated. Further, imaging spectrographs are not particularly suited to record an image of the sample because the recording times—and possibly also the processing times—are frequently as long as several seconds.

It is an object of the invention to provide a device and a method for the measurement of chemical and/or biological samples which make it possible to perform different measurements of a sample, particularly through an image measurement method and a point measurement method, in a simple manner.

SUMMARY OF THE INVENTION

According to one embodiment of the invention, the above object is achieved by the features of an optical measurement device for measurement of chemical and/or biological samples, particularly for use in high throughput screening systems, including: an optical means (22) for imaging a sample area in an image filed (10), a first detector (28) covering a first partial area (12) of the image field (10), and a second detector (34) covering a second partial area (14) of the image field (10). In accordance with another embodiment of the invention, the above object is achieved by the features of an optical measurement device according to the previous embodiment, further characterized in that one of the detectors (28,34,42) is arranged as a focusing means (70) for axial fixation of the sample area imaged in the image field (10). In accordance with yet another embodiment of the invention, the above object is achieved by the features of an optical measurement device for measurement of chemical and/or biological samples (20), particularly for use in high throughput screening systems, including: an optic means (22) for imaging a spatially restricted sample area in a spatially restricted image field (10), a first detector (28) covering a first partial area (12) of the image field (10), and a focusing means (70) for axial fixation of the sample area imaged in the image field (10), comprising a light source (72) generating a focusing beam, the focusing beam extending at least partially within the path of rays (30) generating the image field (10), wherein the illumination means (16) generates the focusing beam.

The invention is based on the recognition that, when imaging a sample area, an image field will always include a part that is not used for examination. In customary optical devices, a round image field 10 (FIG. 1) is generated. Within the image field, e.g. within a first partial area 12 of the image field 10, the field of a CCD camera is arranged. The part of the image field 10 surrounding the first partial area 12 is thus not utilized for the detection of reactions occurring in the sample. The core of the invention resides in that a second partial area of the image field in the unused area of the image field is covered by a second detector.

The inventive optical measurement device which is particularly suited for use in high-throughput screening systems can comprise an illumination unit for illuminating the sample undergoing measurement. Further, an optical device is provided for imaging a sample area in the image field. Further provided is a first detector covering a first partial area of the image field. According to the invention, a second detector is provided which covers the second partial area of the image field.

By the provision of at least two detectors which respectively cover a partial area of the image field, it is possible to perform different measurements simultaneously on a sample. Particularly, it is possible, for instance, to provide the first detector as a CCD camera which is used to perform one of the above described image measurement methods. Then, by means of a second detector, there is preferably performed a point measurement method by which e.g. the development over time of a signal can be recorded.

In the inventive device, the provision of a tiltable mirror for switching between the different detectors used for different measurement methods is not required. As a result, no mechanical wear can occur which might affect the measurement results, particularly the relative position of the two measurement areas in the sample. Further eliminated is the switching process, i.e. the tilting of the mirror, so that the required measurements can be performed in shorter period of time. This is advantageous particularly in case of extremely expensive methods such as high throughput screening. The possibility of simultaneously performing two different measurements on a sample offers the further advantage that effects in a sample which occur only for a short time can be observed also by two measurement methods. When using known devices, the two different measurements have to be carried out successively on two samples.

Thus, according to the invention, there is performed a spatially limited outcoupling of at least one partial area of an image field. This outcoupling is realized preferably by a totally reflecting mirror wherein the outcoupled partial area is covered by a point detector such as e.g. a fiber end. Since the inventive device is particularly suited for application in medium and high throughput screening methods, the device is preferably used to observe individual wells of sample carriers such as titration plates and the like. Thus, preferably, the device will generate an image of a part of the liquid contained in a well while a partial area of this well image is outcoupled. Particularly when providing a totally reflecting mirror for outcoupling the partial area, it is thus possible to detect different areas of the image by use of different detectors, e.g. surface and point detectors. In this regard, no tiltable mirror or dichroic mirror has to be provided. This is advantageous in that, one the one hand, no mechanical wear and the like will occur, and, on the other hand, no expensive dichroic mirror need be used.

Further, with the inventive device, a multi-channel microscopy can be performed in a simple manner. Since the different parts of the image field can be deflected, e.g. by providing mirrors, it is made possible to arrange different filters in the individual paths of rays. The need for an exchange of filters is obviated. Further, filters specially attuned to the requirements can be inserted in the two paths of rays. A provision of expensive combination filters and the like is not required. Further, a considerably larger number of colorants can be used since the latter need not be adapted anymore to a special filter system.

Particularly, in the inventive device, the separation of the two partial areas is not performed on the basis of spectral differences by means of dichromatic mirrors, or sequentially over time by tilting a mirror inwards and outwards.

As measurement methods for image and/or point measurement, all of the above mentioned methods are useful.

According to a preferred embodiment of the invention, the first detector is arranged on the optical axis of an objective of the optics unit. Arranged in the peripheral region of the path of rays generating the image field is a mirror used to outcouple the second partial area and to direct the same to the second detector. This offers the advantage that the second detector does not have to be arranged immediately beside the first detector. Thus, different detectors can be used which would possibly not allow for an arrangement of two detectors immediately side by side, e.g. because a control element of the detector and the like is arranged next to the detector surface.

Of course, it is also possible to arrange the first detector not directly on the axis of the objective but, instead, to deflect also the path of rays by means of mirrors. In any case, in this particular embodiment, the path of rays generating the image field has arranged therein a mirror for outcoupling the second partial area. Preferably, the mirror is arranged to lie outside the path of rays covered by the first detector. Preferably, an overlapping of the individual partial regions is avoided. Since it is safeguarded by the position of the mirror outcoupling the second partial area that this mirror does not extend into the path of rays directed onto the first detector, preferred use can be made of a totally reflecting mirror. Thus, advantageously, the mirror will not affect the radiation detected by the second detector.

Since normally only a relatively small part of the image field is used as a first partial area, the remaining image field can be used by a plurality of detectors. Thus, the image field is divided into a number of two, three, four or more partial regions. Each of these partial regions in turn can be outcoupled via a mirror. Consequently, problems caused by restricted space will be avoided.

Preferably, the further detectors, or the further mirrors for provided to outcouple corresponding partial regions for these detectors, are arranged in such a manner that an overlapping of the partial regions is excluded.

Since, by means of the inventive device, an image measurement as well as a point measurement is performed, at least one of the detectors, preferably the second detector, is designed as a point detector. This detector can be provided e.g. as the open fiber end of an optic fiber. Such a point sensor is useful e.g. for the measurement of the development over time of the fluorescence of material.

In measurement systems with high axial resolution, such as e.g. in confocal microscopes, it is further required that the axial position of the measurement point be reproducibly settable. Particularly in high throughput screening methods, the axial adjustment, i.e. the focusing, has to be performed automatically and quickly. No intervention of operating personal is required because this would occupy too much time and render the high throughput screening methods uneconomical. Since the quality of the received signal is considerably dependent on the axial position, it will normally be necessary to repeat the focusing for each sample under examination.

For focusing, it is possible to use or statistically evaluate the changes in contrast of an image recorded by the detector. Thus, in the inventive device, it is possible to design one of the detectors as a focusing means for axial fixation of the sample area imaged in the image field. Therefore, one of the detectors on which a partial area of the image field is imaged can be used for focusing. This offers the advantage that no additional focusing means are required; such means would normally need a separate light source which would influence the measurement results because this light source would also insert light into the sample.

Further, use can be made of active focusing means which can then have a light source of their own to direct light into the sample for focusing. Also suited is e.g. a light beam obliquely entering the sample to thus generate a fluorescence line in the fluorescing sample. The reflection of this obliquely incident light beam can be used for focusing. A corresponding device is described e.g. in U.S. Pat. No. 6,025,601. Such focusing by means of a line incident on the sample is not useful particularly in case of brightly fluorescing samples. In these samples, the excitation power used should be as small as possible to avoid a bleaching of the sample and possible damage of living cells which may exist in the sample. In this autofocus system, however, a decrease of the excitation power causes also a weakening of the height signal. This leads to a deterioration of the focus setting. Further, such a focusing means can be operated only with relatively small numerical apertures because the incidence of the light occurs at an angle to the optical axis. Thereby, the excitation focus is enlarged so that the axial resolution becomes smaller.

According to a preferred embodiment of the invention, a focusing means with aperture stop is used. By means of the aperture stop, a point of the smallest possible size is illuminated in the sample. The light reflected by this point passes through the same aperture stop to be incident on a detector. Because of the confocality of the arrangement, a focusing is obtained only if a reflecting face in the sample is arranged in the position corresponding to the aperture. If, for instance, the reflection occurs on a glass bottom of a sample carrier having the samples arranged therein, the inventive device allows the focusing onto the glass bottom to be performed in a simple manner. Since the thickness of the glass bottom and the optimum distance between measuring points in the sample and the sample bottom are known, it is possible, after the focusing onto the glass bottom, to safeguard—by a corresponding relative displacement between the sample carrier and the objective—that the measurement within the sample takes place at a predefined distance from the sample bottom. Further, the plane having the aperture stop arranged therein can be selected to the effect that, in case of a reflection signal from the glass bottom through the aperture, the other detectors are arranged to the effect that their focus will be located in the sample area of interest.

Thus, the invention further relates to an optical measurement device comprising an illumination unit and an optics unit as described above. Likewise according to the above description, a first partial area of the image field is covered by a first detector. Instead of or in addition to the second detector, a focusing means is provided for axial fixation of the sample area imaged in the image field. The focusing means comprises a light source generating a focusing beam, with the focusing beam extending at least partially within the path of rays generating the image field. Preferably, a focusing mirror is provided which is arranged in the image-field path of rays after the manner of the above described mirror. Preferably, the arrangement of the mirror is in turn provided such that the mirror will not intersect with the partial area of the image field observed by the first detector, i.e. will not cast a shadow onto the first detector.

Preferably, the focusing means, optionally by use of a correspondingly arranged focusing mirror, is arranged in such a manner that the optics means will direct the focusing beam towards the sample. Preferably, also the focusing beam reflected by the sample or the boundary surface of a sample carrier will be directed by the optics means towards the focusing means and towards the focusing mirror, respectively. The reflection of the focusing beam can take place on different boundary surfaces. For instance, the reflection of the outer surface of the sample carrier can occur on the bottom face of the sample carrier, i.e. the inner side of the bottom of the sample carrier having the sample liquid abutting thereon, or also on the surface of the sample itself, i.e., at the boundary surface between the sample and the surrounding medium, which medium will normally be the air. In dependence from the boundary surface which is used for the reflection of the focusing beam, a corresponding adjustment of the objective means has to be performed to thus ensure that the measurement within the sample will be performed at a corresponding distance from the boundary surfaces. In this manner, an optimum measurement result is guaranteed.

Of course, a combination of the two above described devices is possible so that a plurality of detectors are provided for detecting different partial areas of the image field, and further, a focusing means is provided which preferably covers none of the partial areas of the image field but will utilize the optics means for directing the focusing beam.

The invention further relates to a method for optical measurement of chemical and/or biological samples, particularly by means of high throughput screening systems. According to the inventive method, the sample to be measured can be illuminated. Subsequently, using an optics means, a sample area is imaged in an image field. Both the sample area and the image field are spatially limited regions. In a first partial area of the image field, the image which is imaged in the partial area is taken up by a first detector. Further, a second partial area of the image field is taken up by a second detector. This method has the same advantages over known methods which have been explained in connection with the above described inventive device.

Preferably, in the inventive method, not only two but three, four, five or more partial areas are of the image field are covered. The individual partial areas will preferably not overlap.

BRIEF DESCRIPTION OF THE DRAWINGS

The invention will be explained hereunder on the basis of preferred embodiments and with reference to the accompanying drawings.

In the drawings.

DETAILED DESCRIPTION OF THE INVENTION

Figure 1:
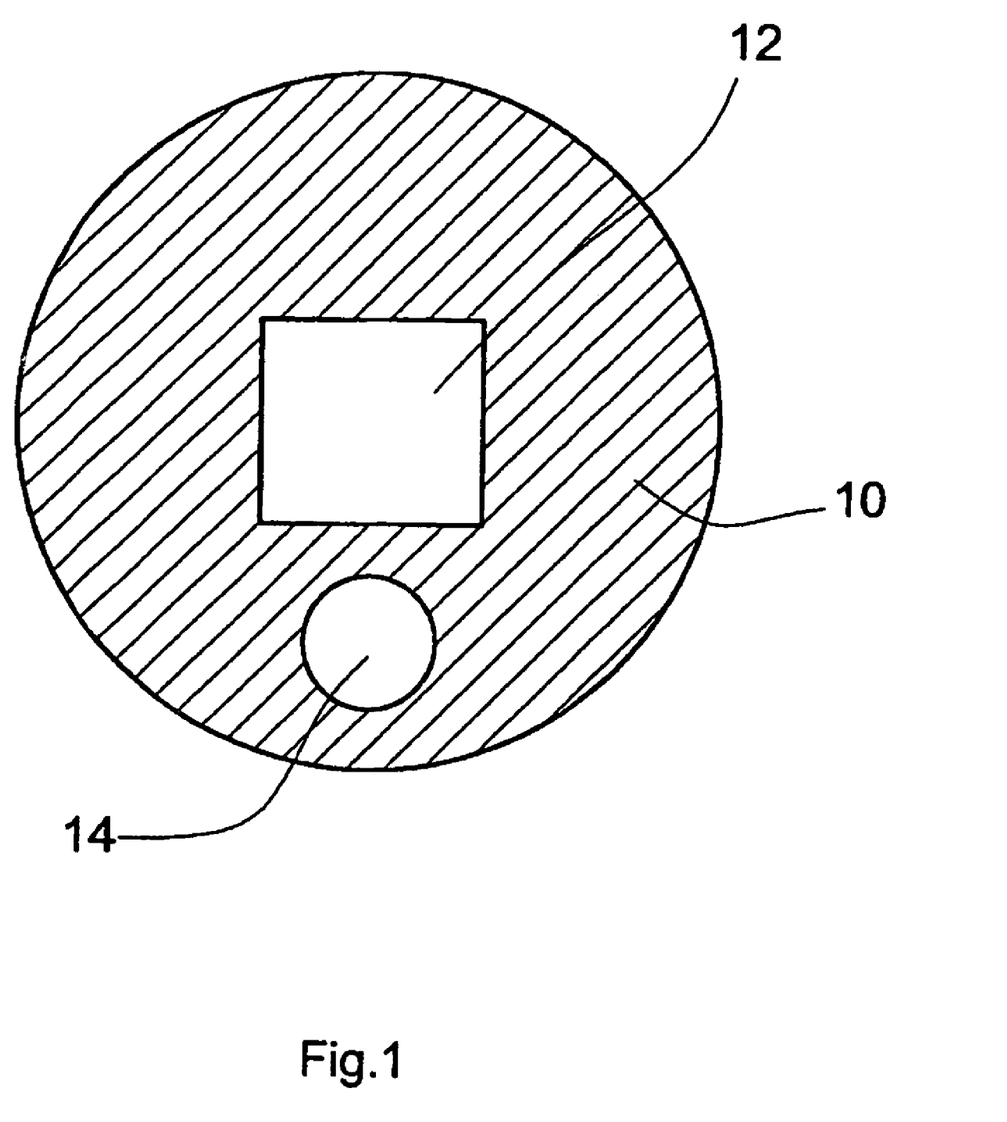
FIG. 1 is a schematic view of an image field.

FIG. 1 shows an image field 10 as normally generated in an optics means used in microscopes and the like. Usually, image field 10 is provided as a circular two-dimensional region. Within image field 10, a first partial area 12 is provided. In the illustrated example, the first partial area 12 is a rectangular partial area, e.g. the camera field of a CCD camera. A second partial area 14 is also arranged within image field 10. In the illustrated example, the second partial area 14 is represented as a circle. This is normally a partial area where a point measurement is performed. The detector is provided e.g. as an optical fiber so that the partial area 14 has the fiber end of an optical fiber arranged therein.

Figure 2:
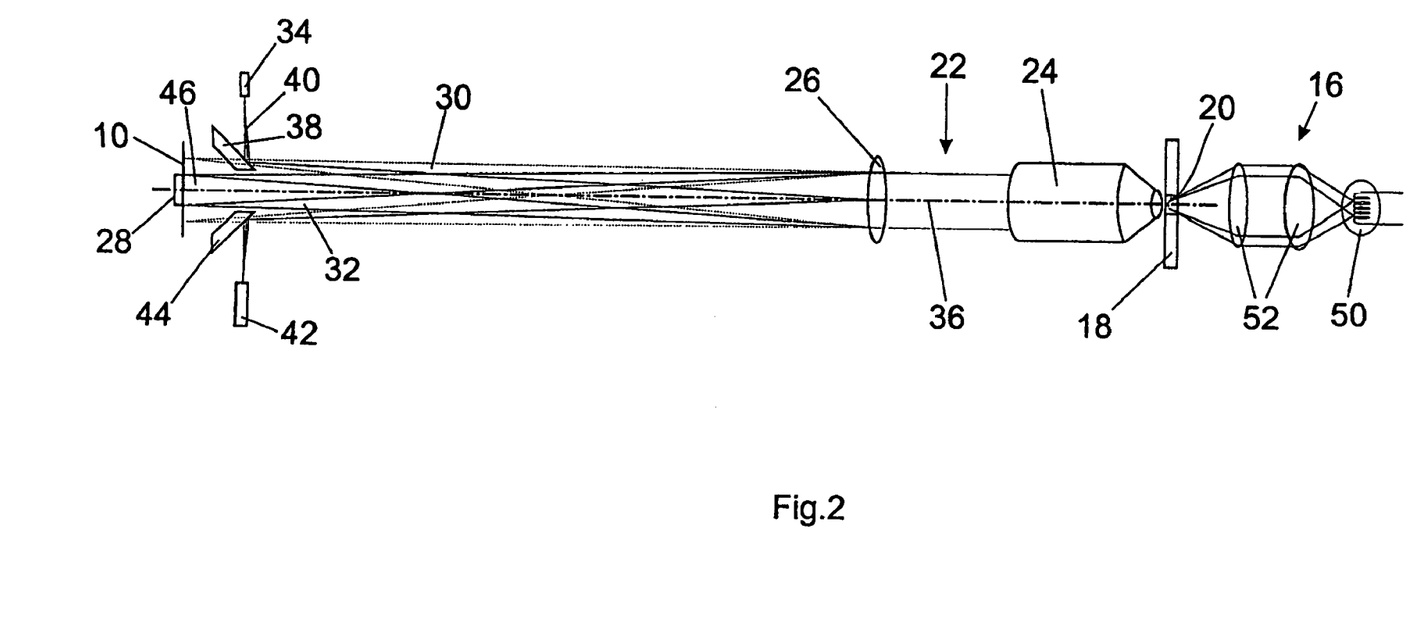
FIG. 2 is a schematic view of a preferred embodiment of the invention with three detectors.

The schematic configuration of the inventive optical measurement device (FIG. 2) comprises an illumination means 16 for illuminating a sample 20 arranged e.g. in a titration plate 18. The light emitted from sample 20 or the radiation emitted from sample 20 is guided, by an optics means 22 comprising an objective 24 and at least one tubular lens 26, in the direction of a first detector 28. In an image plane arranged at the height of detector 28, the image field 10 (FIG. 1) is generated. The image field is generated by a path of rays 30 marked by hatched lines. The first detector 28 covers the first partial area 12 (FIG. 1). The latter is delimited by a first path of rays 32 which is part of the image-field path of rays 30.

In the illustrated example, a second detector 34 provided to cover the second partial area 14 of image field 10 (FIG. 1) is arranged at a rotation of 90° relative to an optical axis 36. To direct the relevant part of the image-field path of rays 30 towards the second detector 34, a totally reflecting mirror 38 is provided. Mirror 38 outcouples a part 40 of the image-field path of rays 30 and directs this part to the second detector 34.

Opposite the second detector 34, a further—third—detector 42 can be arranged. The third detector 42 is arranged vertically to the optical axis 36 as is the case for the second detector 34. The third partial area of image field 10 imaged on the third detector 42 is outcoupled from the image-field path of rays 30 by a mirror 44. Of course, the third detector 42 together with the mirror 44 can also be arranged in a different orientation and cover a different partial area of the image field 10.

In the invention, it is essential that the partial area 12 imaged onto the first detector 28 and generated by a path of rays 46, is not influenced by the second and third detector 34,42. As can be seen from FIG. 2, the path of rays 46 extends between the two mirrors 38,44 so that none of the mirrors 38,44 can project into the path of rays 46 and thus affect the part of the sample 20 which is imaged onto the first detector 28.

The illumination means 16 comprises a light source 50 and a lens arrangement 52. By the lens arrangement 52, the light emitted by light source 50 is caused to converge onto the sample so that a concentration of light occurs in the sample 20. In the illustrated embodiment, the illumination means 16 is arranged opposite the objective unit 22 so that the sample is illuminated from the side opposite the objective unit 22. This is a case of a so-called transmission illumination. Further, it is possible to illumine the sample 20 by use of incident illumination. For this purpose, light emitted by a light source is coupled into the objective 24 by a corresponding lens and mirror arrangement and is directed from the objective into the sample.

The first detector 28 can be e.g. a CCD or CMOS camera. When combined with a suitable line illumination, the first detector 28 can also be a line camera. Further, the detector can be provided as a spectrograph.

For the second detector, use can be made of a detector corresponding to the first detector or a combination of the above described detectors. Further, the possibility exists to provide one or several of the detectors 28,34,42 e.g. as a fluorescence emission spectroscope, optionally in combination with suitable filters. Further, the detectors can be designed as FCS or FIDA detectors.

Figure 3:
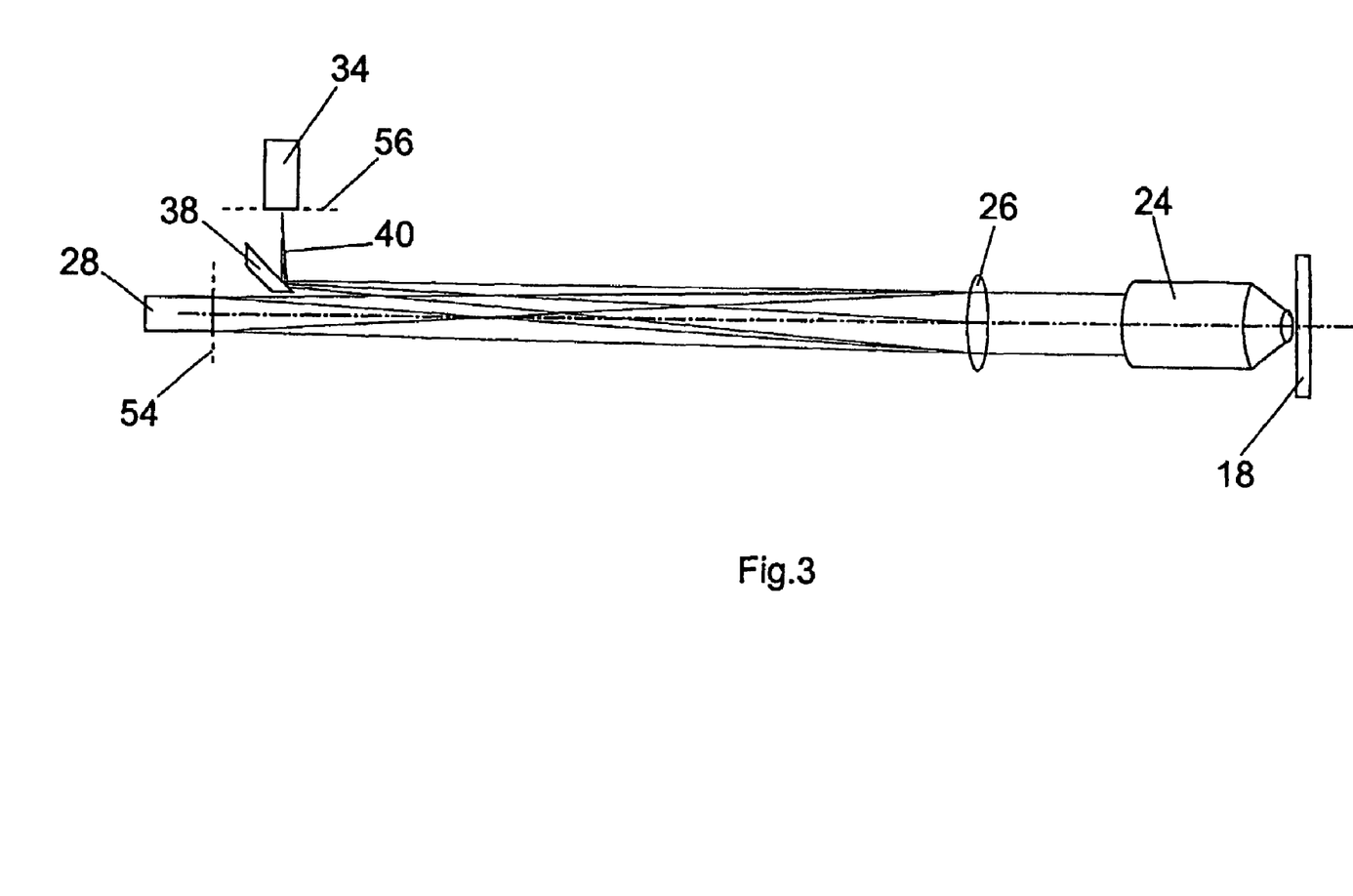
FIGS. 3-5 are schematic views of possible arrangements of the second detector.
Figure 4:
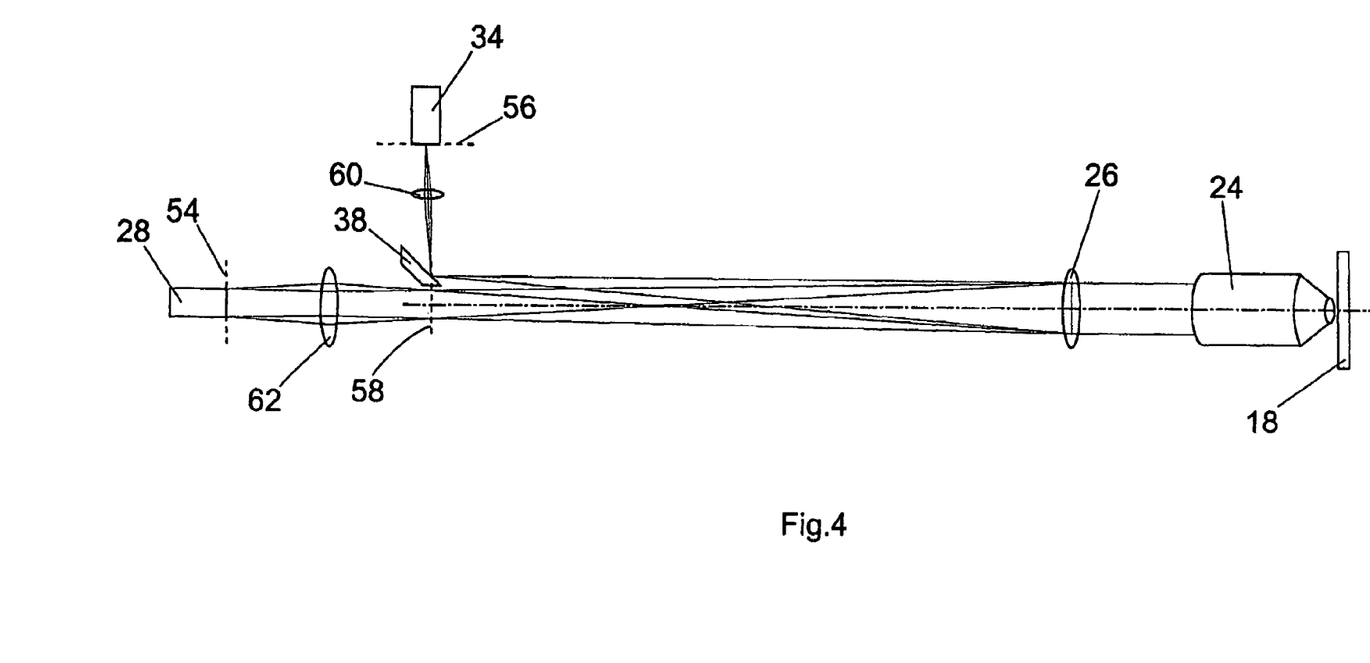
Figure 5:
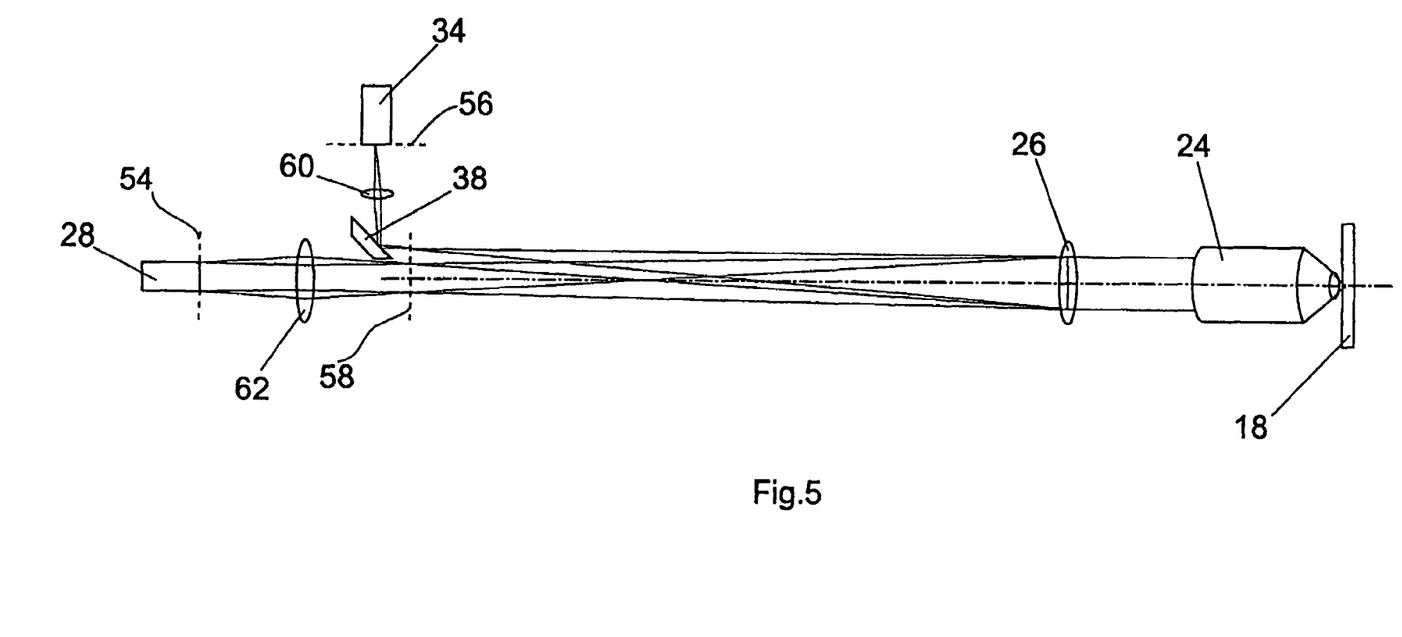

In FIGS. 3-5, different possibilities for the arrangement of the second detector 34 are illustrated. The illumination means 16 is not shown in these Figures.

In FIG. 3, the mirror 38 is located in front of an image plane 54 having the image field 10 arranged therein. The deflection of a bundle of rays 40 is performed in the manner described above with reference to FIG. 2. The second detector 34 is arranged in an image plane 56 which is a part of image plane 54 which has been deflected by mirror 38.

Further, it is possible to arrange the mirror 38 in an intermediate image plane 58 (FIG. 4). To arrange the detector 34 in the image plane 56, a lens 60 is provided between the mirror 38 and the detector 34. Correspondingly, a further lens 62 is provided between the intermediate image plane 58 and the image plane 54 for imaging the first partial area 10 onto the detector 28. If the detectors 28,34 do not require an imaging of the sample (e.g. in case of point intensity measurements or direct coupling into a spectrograph), the lenses 60,62 can also be omitted.

As illustrated in FIG. 5, it is also possible to arrange the mirror 38 behind the intermediate image plane 58 when viewed along the path of rays. According to FIG. 4, the lens 60 is again arranged between the mirror 38 and the image plane 56 of detector 34.

Figure 6:
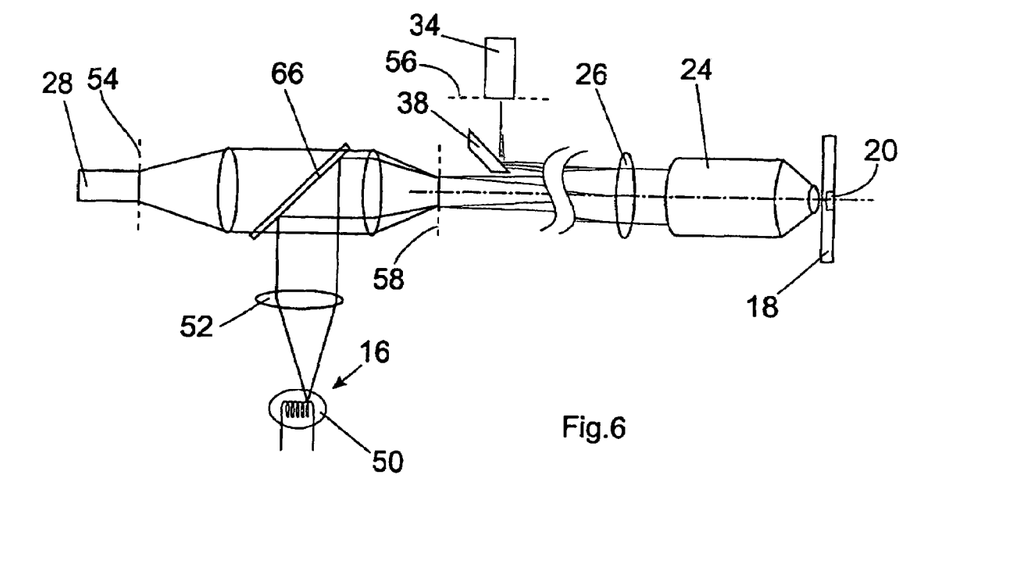
FIGS. 6-8 are schematic views of possible configurations of the first detector together with an illumination means.
Figure 7:
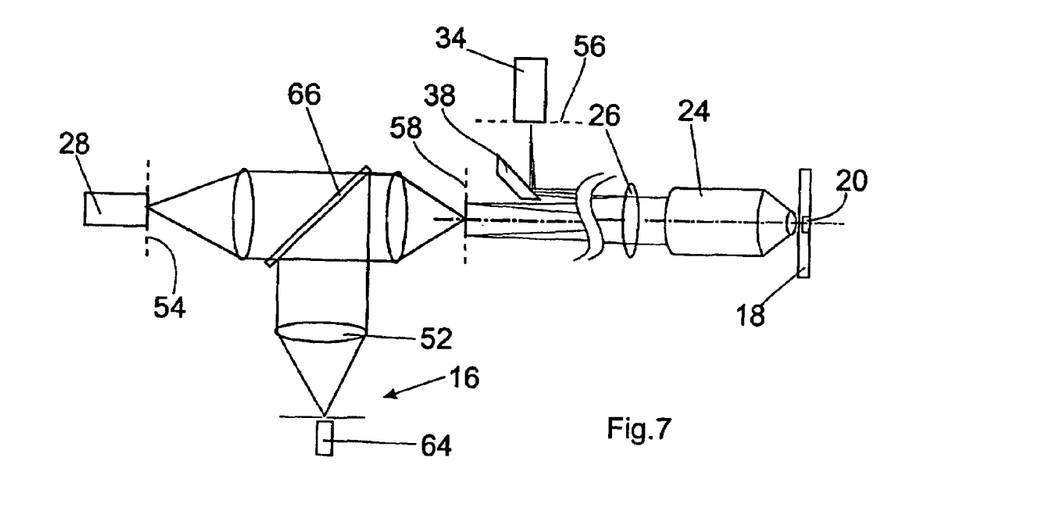
Figure 8:
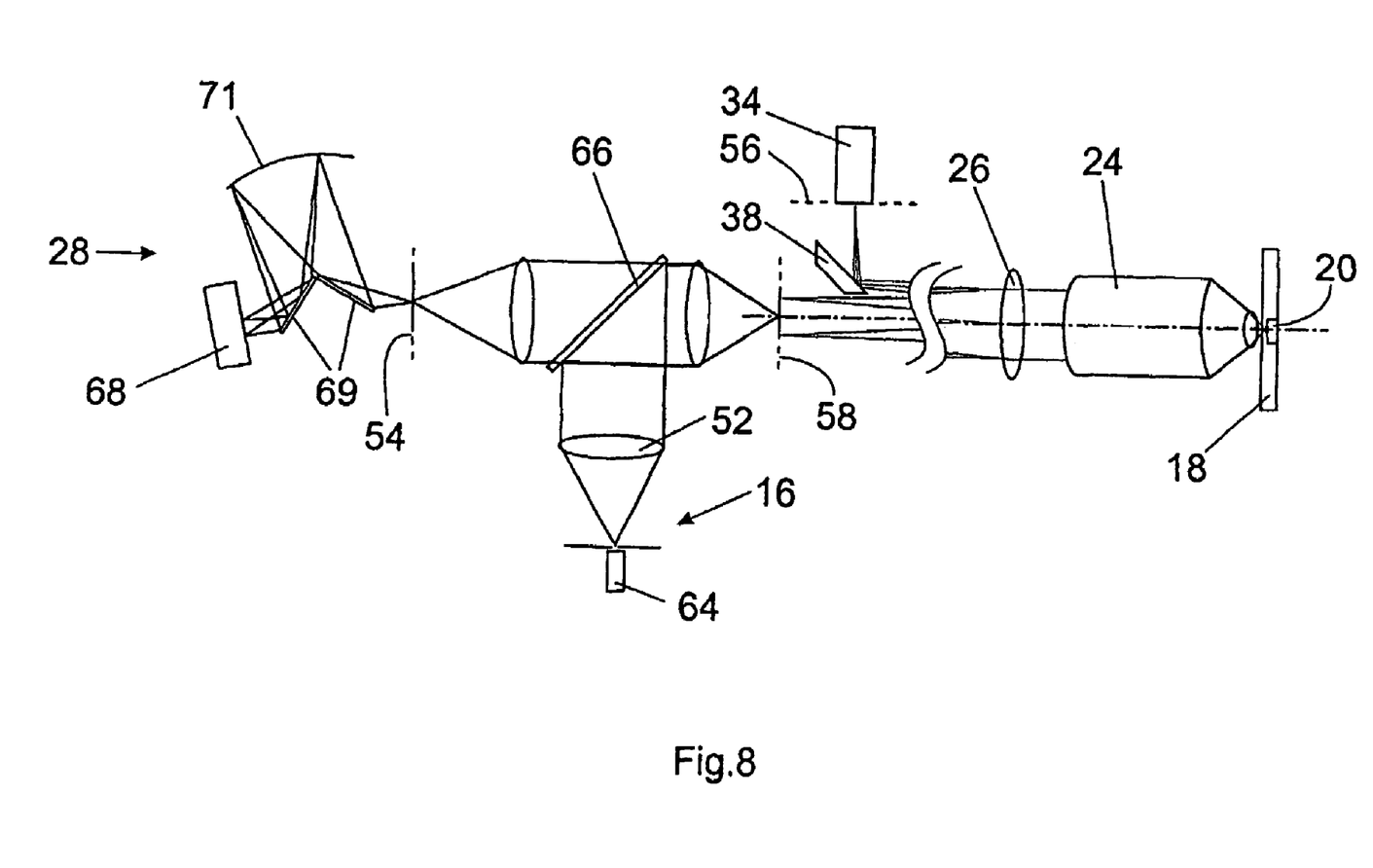

In FIGS. 6-8, the illumination means 16 is arranged respectively between the intermediate image plane 58 and the image plane 54. The illumination means comprises a lens or lens arrangement 52. The light emitted by the light source 50 which can also be a line illumination means 64 (FIGS. 7 and 8) is coupled, by means of a partially transmitting or dichromatic mirror 66, into the path of rays extending between the objective 24 and the first detector unit 28. In the embodiments according to FIGS. 6-8, the second detector 34 together with mirror 38 is in each case arranged in front of the intermediate image plane 58.

In FIG. 6, the conventional light source 50 is combined with a CCD or CMOS camera serving as a first detector 28. In FIG. 7, a line illumination means 64 is provided in combination with a line detector as a first detector 28. To obtain a complete image of a sample plane, the line has to be moved relative to the sample 20. This is done either by moving the sample or by moving the light beam incident into the sample, e.g. by an oscillating mirror. Instead of using a line camera as a first detector 28, the latter can also be provided as an imaging spectrograph (FIG. 8). This spectrograph comprises, apart from an image take-up device 68, a mirror arrangement including two planar mirrors 69 and a hollow mirror 71. The planar mirrors 69 can be tilted relative to each other.

Figure 9:
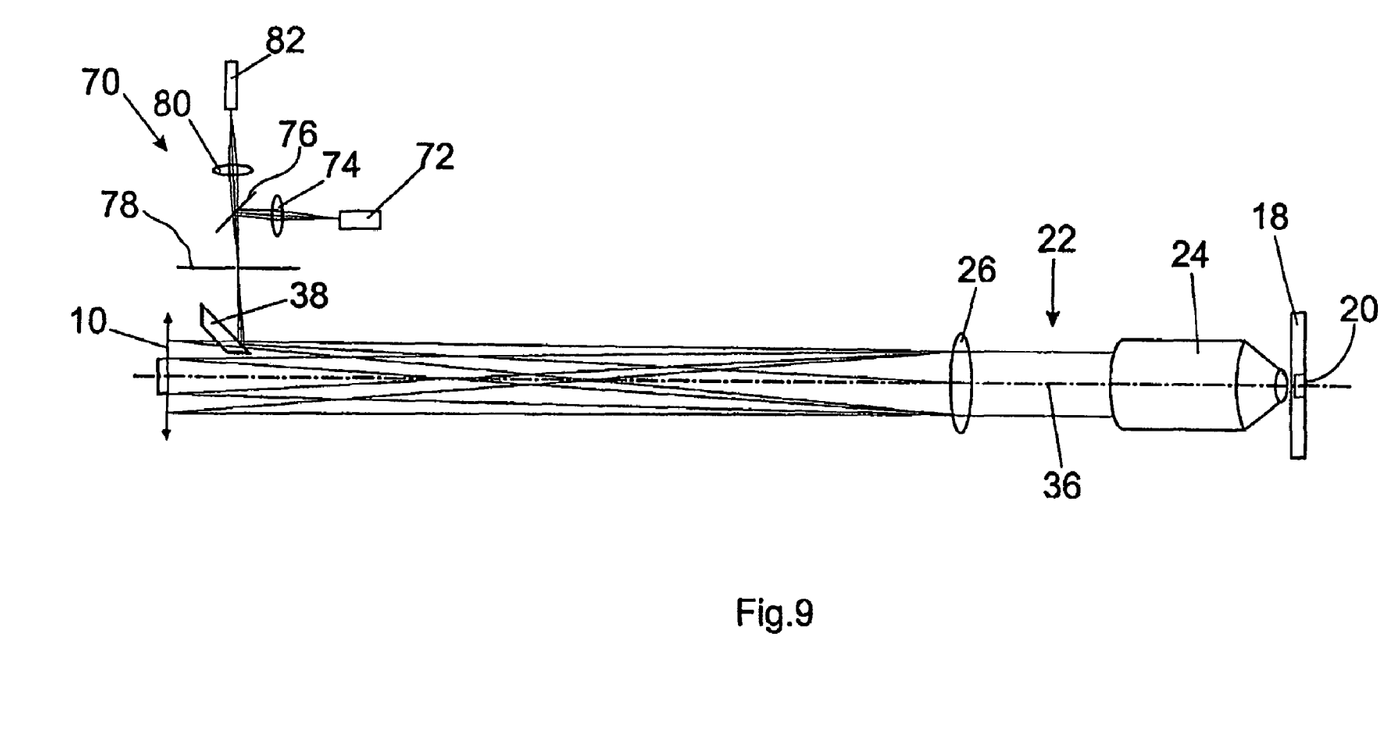
FIG. 9 is a schematic view of a further preferred embodiment of the invention in combination with a focusing means.

In the embodiment shown in FIG. 9, a focusing means 70 is provided instead of the second detector 34. Of course, one or a plurality of detectors 34,42 can be provided in addition to the focusing means 70. Mirror 38 is arranged in the manner described above and particularly evident from FIG. 2. From a light source 72, light is guided via a lens 74 to a partially transmitting mirror 76. From this mirror, the light is deflected towards an aperture stop 78. The aperture stop is arranged in or near an image plane. Thereby, a point in the sample is illuminated. The light reflected from this point in the sample is directed, again via mirror 38, towards the aperture stop 78. After passing the aperture stop 78, the light returning from sample 20 is allowed to pass through the partially transmitting mirror 76 and is guided via a lens 80 to a detector 82. By means of the illustrated focusing means, a focusing is possible onto a reflecting face of the sample, e.g. a boundary surface of the titration plate or a surface of the sample. With corresponding focusing, a maximum of the light reflected by the sample will pass through the aperture stop and reach the detector 82. If it is known that a focusing has been performed onto the glass bottom of a sample carrier 18, the optics unit can then be shifted by a specific amount so that the image field 10 will show an area arranged within the sample. Further, the aperture stop 78 can be moved out of the image plane 56 to such an extent that a signal on detector 82 is accompanied by the focusing of the sample area of interest onto the detector 28.

Also other focusing means can be contemplated wherein the focusing is performed e.g. on the basis of the contrast or a fluorescence line generated in the sample.

The focusing sensors can be provided e.g. as 2×2 phase couplers. In this case, the fiber itself can be used as the aperture determining the autofocal measurement site. Further, an additional aperture stop can be used. In screening systems, such as line detectors, the measurement point for the autofocus can also be arranged in front of the line when viewed in the scanning direction. In this case, it is possible to carry out the height control, without phase shifting, in a control loop since the measurement point takes up the measurement value at a position which the actual detector will reach only later.

Since the autofocus measurement point is arranged beside the area covered by the image detector, a correction of the height corresponding to the oblique orientation of the sample appears useful. Such a correction is reasonable whenever a lateral displacement of measurement points occurs.

As evident particularly from the Figures, a substantial feature of the invention resides in that the outcoupling mirror and the detectors, respectively, i.e. the fibers or other point detectors, are arranged before, in or behind the image plane. Particularly, the detectors are arranged near the image plane.

The invention claimed is:

1. An optical measurement device for measurement of chemical and/or biological samples, particularly for use in high throughput screening systems, comprising:
   an optical means for imaging a sample area in an image field;
   a first detector covering a first partial area of the image field; and
   a second detector covering a second partial area of the image field, wherein the second partial area is a different area from the first partial area so that the first partial area is detected by the first detector and the second partial area is detected by the second detector.

2. The optical measurement device according to claim 1, characterized by an illumination means for illuminating the sample to be measured.

3. The optical measurement device according to claim 2, characterized in that the first detector is arranged on the optical axis of an objective of the optics unit.

4. The optical measurement device according to claim 1, characterized in that the first detector is arranged on the optical axis of an objective of the optics unit.

5. The optical measurement device according to claim 1, characterized in that the path of rays generating the image field has arranged therein a mirror for outcoupling the second partial area.

6. The optical measurement device according to claim 5, characterized in that the mirror is totally reflecting.

7. The optical measurement device according to claim 1, characterized by further detectors for detecting further partial areas of the image field.

8. The optical measurement device according to claim 1, characterized in that the partial areas do not overlap.

9. The optical measurement device according to claim 1, characterized in that at least one detector is a point detector.

10. The optical measurement device according to claim 9, characterized in that the point detector is an open fiber end of an optical fiber.

11. The optical measurement device according to claim 1, characterized in that the optics means comprises only one objective.

12. The optical measurement device according to claim 1, characterized in that one of the detectors is arranged as a focusing means for axial fixation of the sample area imaged in the image field.

13. The optical measurement device according to claim 1, characterized by a focusing means.

14. The optical measurement device according to claim 1, further comprising a third detector covering a third partial area of the image field, wherein the third partial area is a different area from each of the first partial area and the second partial area so that the third partial area is detected by the third detector.

15. The optical measurement device according to claim 1, wherein the first detector is a camera or spectrograph and the second detector is a point detector.

16. A method for optical measurement of chemical and/or biological samples, particularly by use of high throughput screening systems, comprising the following steps:
   imaging a sample area in an image field;
   covering a first partial area of the image field by a first detector; and
   covering a second partial area of the image field by a second detector, wherein the second partial area is a different area from the first partial area so that the first partial area is detected by the first detector and the second partial area is detected by the second detector.

17. The method according to claim 16 wherein the sample is illuminated.

18. The method according to claim 16, wherein further partial areas of the image field are covered.

19. The method according to claim 16, wherein the sample area to be imaged is focused in the image field.

20. The method according to claim 19, wherein a focusing beam is generated which extends at least partially within a path of rays generating the image field.

21. The method according to claim 16, further comprising the step of:
   covering a third partial area of the image field by a third detector, wherein the third partial area is a different area from each of the first partial area and the second partial area so that the third partial area is detected by the third detector.

22. The method according to claim 16, wherein the first detector is a camera or spectrograph and the second detector is a point detector.

* * * * *